CHRYSANTHEMUM PLANT
Filed April 25, 1975
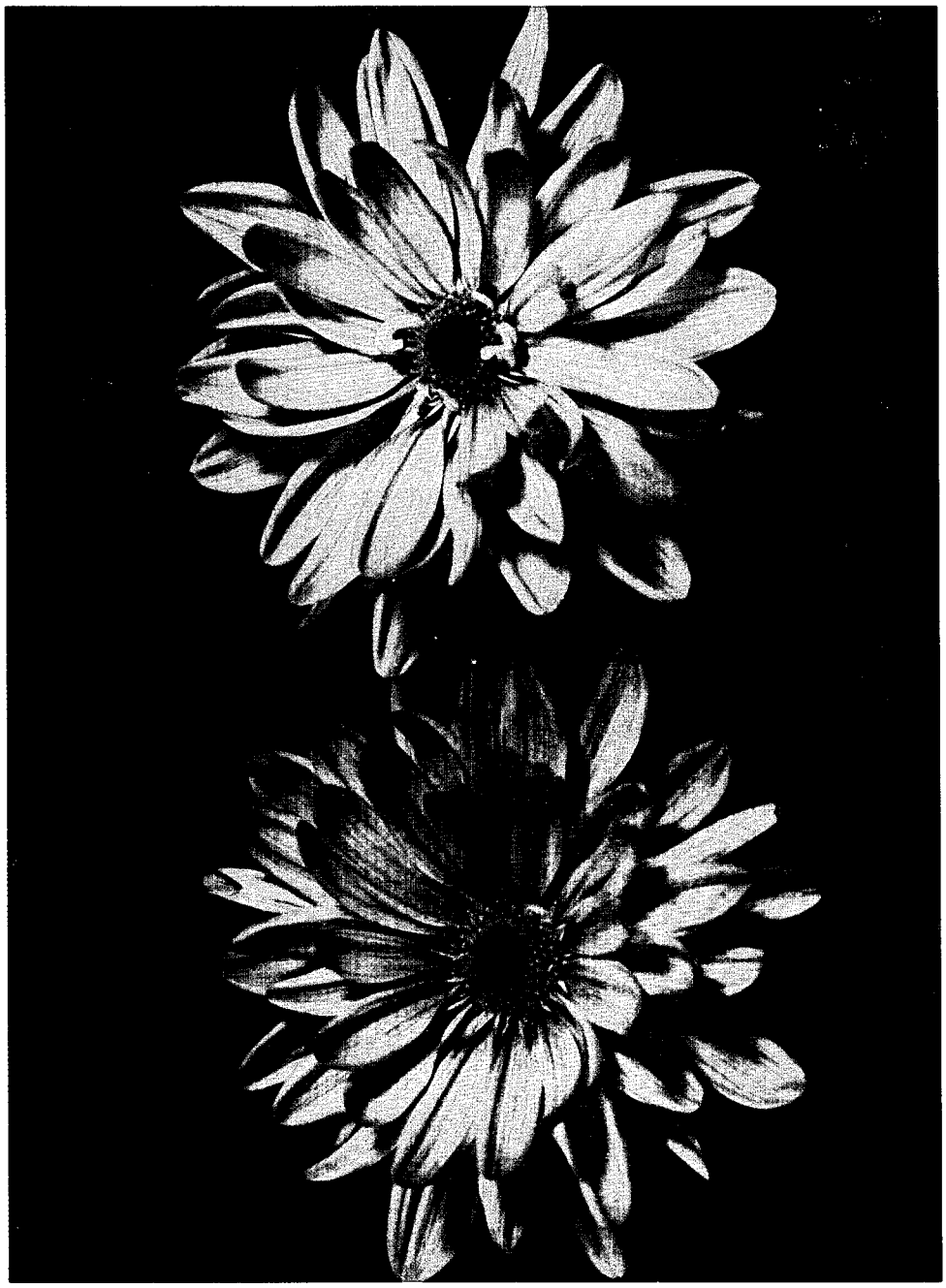

United States Patent

Plant Pat. 3,903
Patented June 8, 1976

3,903

CHRYSANTHEMUM PLANT

Walter H. Jessel, Jr., Doylestown, and William Erwin Duffett, Akron, Ohio, assignors to Yoder Brothers, Inc., Barberton, Ohio

Filed Apr. 25, 1975, Ser. No. 571,478
Int. Cl. A01h *5/00*
U.S. Cl. Plt.—74 1 Claim

The present invention comprises a new and distinct cultivar of *Chrysanthemum morifolium,* Ramat., hereinafter referred to by the cultivar name Senora (#70044D08).

Senator is an induced sport of the cultivar Senorita (#70044008; commercially available; U.S. Plant Pat. #3,629). Senora was discovered and selected by William E. Duffett and Walter H. Jessel, Jr. on August 4, 1972 as one plant within a flowering block of the parental cultivar in a controlled environment in Barberton, Ohio. Plants in the flowering block were derived from stock plants which had been irradiated as unrooted cuttings by an X-ray source of 188 r. units.

Senora is a product of a planned sport induction program which had the objective of expanding the color range of Senorita, a lavender pink daisy. Senorita was originated by the present inventors in the year 1970 as a product of a controlled breeding program. Senorita was discovered and selected from the progeny of an unidentified cross.

The first act of asexual reproduction of Senora was accomplished when vegetative cuttings were taken from the initial selection in December 1972 in a controlled environment in Barberton, Ohio by a technician working under formulations established and supervised by William E. Duffett and Walter H. Jessel, Jr. Horticultural examination of selected units initiated Apr. 2, 1973 has demonstrated that the combination of characteristics as herein disclosed for Senora are firmly fixed and are retained through successive generations of asexual reproduction.

Senora has not been observed under all possible environments. The phenotype may vary significantly with variations in environment such as temperature, light intensity, and daylength. The following observations, measurements, and comparisons describe pinched, disbudded plants grown in a greenhouse in Barberton, Ohio under environmental conditions which closely approximate those generally used in commercial practice, as described in Chart A and Chart B which appear at the end of the present specification.

The following traits have been repeatedly observed and which in combination distinguish this chrysanthemum as as new and distinct cultivar:

(1) Daisy inflorescence type.
(2) Semi-incurved inflorescence form.
(3) Diameter across face of inflorescence from 5.5 to 6.5 inches at maturity.
(4) Bronze ray floret color.
(5) Tall plant height.
(6) Uniform 9 week flowering response period.
(7) Semi-spreading branching habit.

The accompanying photographic drawing depicts the distinguishing feature of bronze ray floret color of Senora in comparison to the lavender pink ray floret color of the parental cultivar, Senorita. Color representation is as true as possible with color photographs of this type.

Of the many commercial cultivars known to the present inventors, the most similar existing culivars in comparison to Senora are Senorita, Dramatic (#67079001; U.S. Plant Pat. #3,189), and Dixie (#700040039; U.S. Plant Pat. #3,655). Reference is made to attached Chart C which compares certain characteristics of the above mentioned cultivars with the same characteristics of Senora. General comparisons are as follows:

(1) In comparison to Senorita, Senora has bronze ray floret color. The inflorescence form and type, diameter across face of inflorescence, branching habit, plant height, and flowering response period of Senora are similar to those of Senorita.

(2) In comparison to Dramatic, Senora has more incurved inflorescence form, less yellow ray floret color, larger diameter across face of inflorescence, more spreading branching habit, and longer flowering response period. The inflorescence type and plant height of Senora are similar to those of Dramatic.

(3) In comparison to Dixie, Senora has more incurved inflorescence form, less orange ray floret color, larger diameter across fact of inflorescence, taller plant height, and longer flowering response period. The inflorescence type and branching habit of Senora are similar to those of Dixie.

In the following description, color references are made to The Munsell Limit Color Cascade, 1972 edition. The color values were determined between 10:30 and 11:00 a.m. on Jan. 23, 1975 under 130 foot candle light intensity at Barberton, Ohio.

Botanical classification: *Chrysanthemum morifolium*, Ramat., cv Senora.

C. Foliage:

*Color (abaxial)*.—20–14 to 20–15 with less olive green.

*Color (adaxial)*.—20–13 overcast with white.

*Shape*.—Spatulate; deeply lobed.

*Texture*.—Glabrous.

*Arrangement*.—Alternate.

*Veination*.—Prominent.

*Margin*.—Moderately serrated.

CHART A.—AVERAGE GREENHOUSE CHRYSANTHEMUM ENVIRONMENTS USED FOR BARBERTON, OHIO

| Season | Temperatures used,° F. | | | Lighting used | Black cloth used | Supp., $CO_2$ |
|---|---|---|---|---|---|---|
| | Night | Bright day | Cloudy day | | | |
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15, 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15, 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

I. INFLORESCENCE

*Form*.—Semi-incurve.

*Type*.—Daisy.

*Permanence*.—12–14 days.

Diameter across face.—5.5 to 6.5 inches.

B. Corolla of ray florets:

*Texture (adaxial)*.—Glabrous.

*Appearance and form*.—Ligulate.

*Arrangement*.—Whorled on receptacle.

*Persistence*.—Resists shatter.

*Color (abaxial)*.—28–4 to 28–5 streaked with 33–13 (duller).

*Color (adaxial)*.—28–3 streaked with 33–5 (duller).

C. Corolla of disc florets: Gamopetalous; tubular; 5-lobed.

*Color*.—23–10 to 17–6.

D. Reproductive organs:

*Androecium*.—Present disc florets only; synegesious stamen; abundant to scant pollen (functional sterility).

*Gynoecium*.—Present both ray and disc florets; inferior, bicarpellate ovary; single style; 2-lobed stigma.

II. PLANT

A. General appearance: Semi-spreading; tall.

B. Duration and texture: Herbaceous; perennial.

CHART B

INTENSITY OF DIRECT SOLAR RADIATION

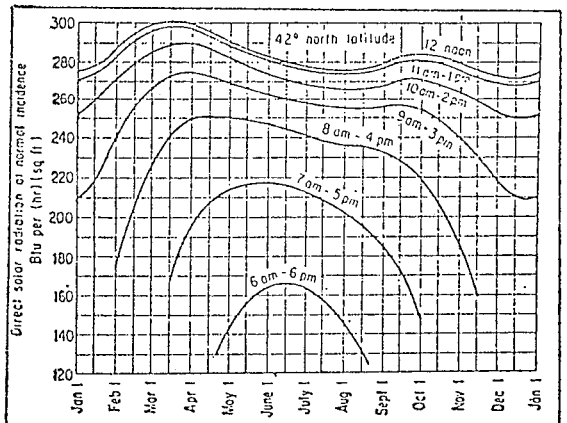

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C.—COMPARISON OF SENORA, SENORITA, DRAMATIC AND DIXIE

| Cultivar | Inflorescence form and Type | Inflorescence color | Diameter across face of inflorescence, inches | Branching habit | Plant height | Flowering response |
|---|---|---|---|---|---|---|
| Senora | Semi-incurved daisy | Bronze | 5.5 to 6.5 | Semi-spreading | Tall | 9 weeks. |
| Senorita | do | Lavender pink | 5.5 to 6.5 | do | do | Do. |
| Dramatic | Flat daisy | Golden bronze to yellow | 2.5 to 3.5 | Semi-upright | do | 8 weeks. |
| Dixie | do | Orange bronze | 3.25 to 4.0 | Semi-spreading | Medium | Do. |

NOTE.—Comparisons made of pinched, disbudded plants grown in a greenhouse in Barberton, Ohio, under conditions as described in Chart A and Chart B.

We claim:

1. A new and distinct cultivar of chrysanthemum plant characterized particularly by the combined characteristics of daisy inflorescence form and semi-incurved inflorescence form, 5.5 to 6.5 inches diameter across face of inflorescence at maturity, bronze ray floret color, tall plant height, uniform 9 week flowering response period, and semi-spreading branching habit.

No references cited.

ROBERT E. BAGWILL, Primary Examiner